US010353038B2

United States Patent
Grodzki et al.

(10) Patent No.: US 10,353,038 B2
(45) Date of Patent: Jul. 16, 2019

(54) MAGNETIC RESONANCE METHOD AND APPARATUS FOR ACCELERATING MAGNETIC RESONANCE FINGERPRINTING

(71) Applicant: Siemens Aktiengesellschaft, Munich (DE)

(72) Inventors: David Grodzki, Erlangen (DE); Esther Raithel, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 697 days.

(21) Appl. No.: 14/943,496

(22) Filed: Nov. 17, 2015

(65) Prior Publication Data
US 2016/0139227 A1    May 19, 2016

(30) Foreign Application Priority Data
Nov. 17, 2014  (DE) .................. 10 2014 223 388

(51) Int. Cl.
*G01R 33/56*    (2006.01)
*G01R 33/48*    (2006.01)
*A61B 5/055*    (2006.01)

(52) U.S. Cl.
CPC .......... *G01R 33/5608* (2013.01); *A61B 5/055* (2013.01); *G01R 33/4828* (2013.01)

(58) Field of Classification Search
CPC .. G01R 33/5608; G01R 33/4828; A61B 5/055
See application file for complete search history.

(56) References Cited

U.S. PATENT DOCUMENTS 8,344,730 B2 * 1/2013 Kimura ............... A61B 5/0275
                                                    324/318
2009/0226060 A1 * 9/2009 Gering ..................... G06T 7/11
                                                    382/128

(Continued)

OTHER PUBLICATIONS

Cauley et al.: "Fast Group Matching for MR Fingerprinting Reconstruction";: Magn. Reson.Med. vol. 74; pp. 523-528; (2015).

(Continued)

*Primary Examiner* — Huy Q Phan
*Assistant Examiner* — Dustin R Dickinson
(74) *Attorney, Agent, or Firm* — Schiff Hardin LLP (57) ABSTRACT

In a method and apparatus for the examination of a predetermined volume portion of an object with a magnetic resonance (MR) fingerprinting procedure, an MR signal curve for voxels of the volume portion is acquired, and a comparison of the MR signal curve of the respective voxel is made with stored MR signal curves in order to determine the stored MR signal curve that conforms most closely to the MR signal curve, with the result of the comparison then being made available as an output. The comparison with the MR signal curve of the voxel is (initially) performed with a specific number of signal points of the MR signal curve. A quality measure is determined with which the quality of the most closely conforming stored MR signal curves is determined. The performance of the comparison for the respective voxel is repeated if the quality measure is below a predetermined quality threshold value, with the number of signal points being first increased by a difference number.

15 Claims, 3 Drawing Sheets

(56) References Cited

U.S. PATENT DOCUMENTS

| | | | |
|---|---|---|---|
| 2011/0299747 A1* | 12/2011 | Solf | A61B 6/00 382/128 |
| 2013/0265047 A1* | 10/2013 | Griswold | G01R 33/56 324/309 |
| 2014/0126789 A1* | 5/2014 | Ban | G06T 7/337 382/128 |
| 2014/0309519 A1* | 10/2014 | Huang | A61B 5/015 600/411 |
| 2015/0297101 A1* | 10/2015 | Hernandez-Garcia | G01R 33/56563 600/419 |
| 2015/0346301 A1* | 12/2015 | Cauley | G01R 33/50 324/309 |

OTHER PUBLICATIONS

Ma et. al,.: "Magnetic Resonance Fingerprinting", Nature. vol. 495, No. 7440, pp. 187-192; (2013;).

McGivney et al.:"SVD Compression for Magnetic Resonance Fingerprinting in the Time Domain"; IEEE Trans. Med. Imaging vol. 33; pp. 2311-2322 (2014).

Davies et.al.:"A compressed sensing framework for Magnetic Resonance Fingerprinting"; //arxiv.org/abs/1312.2465; Version of Jun. 6, 2014; (2014).

Cohen et al. "15T ultrahigh field fast MR fingerprinting with optimized trajectories"; 55th Experimental NMR Conference, Boston USA;; (2014).

\* cited by examiner

FIG 1

MAGNETIC RESONANCE METHOD AND APPARATUS FOR ACCELERATING MAGNETIC RESONANCE FINGERPRINTING

BACKGROUND OF THE INVENTION

Field of the Invention

The present invention concerns an examination of an object with a magnetic resonance (MR) system by MR fingerprinting.

Description of the Prior Art

In clinical imaging, MR images generally have only a qualitative contrast. The exact pixel values are subject to many influences, such as the parameter settings selected for the measurement (e.g. TE, TR, bandwidth) and factors that the user is unable to influence (e.g. coil sensitivity, software versions, scanner type).

In many applications, it would be desirable to have a so-called quantitative MR image in which the pixel values would correspond to "genuine" physical variables (for example the T1 relaxation time, the T2 relaxation time, the off-resonance, the proton density). One quantitative MR imaging method of this kind is so-called MR fingerprinting, which is described in "Magnetic Resonance Fingerprinting", Ma et al, Nature 2013 Mar. 14; 495(7440): 187-192. doi: 10.1038/nature11971. With MR fingerprinting, numerous measurements are performed wherein measuring parameters or recording parameters (e.g. flip angle, TR (time to repetition), TE (echo time), TI (inversion time), an embodiment and/or a number of RF pulses, an embodiment and/or a number of gradient pulses, diffusion encoding) are varied in a pseudo-random manner. For each measurement, the MR signal is determined for each voxel so that for each voxel or pixel an MR signal curve characterizing the voxel or pixel is obtained, which can be considered to a "fingerprint". A fingerprint of this kind can be assigned, with the use of a database, to a specific n-tuple of physical values (e.g. T1 relaxation time, T2 relaxation time, off-resonance, proton density), and hence to a specific substance (e.g. CSF, cerebral grey matter, fat).

The database stores MR signal curves for the pseudo-random variation of the recording parameters for many of these n-tuples of physical values. These stored MR signal curves are usually generated by simulation with the use of Bloch equations on the basis of the pseudo-random variation of the recording parameters. In order, for example, to have an MR signal curve for each combination of a T1 relaxation time in a range of from 100 ms to 5000 ms and a T2 relaxation time in a range of from 10 ms to 2000 ms with a resolution of 10 ms, it is necessary for as many as almost 100,000 MR signal curves to be available.

Pattern recognition algorithms are now used to determine the stored or simulated MR signal curve conforming most closely to the respective MR signal curve measured for a specific voxel or pixel.

According to the prior art, the number of MR images to be recorded, and hence the length of the MR signal curve measured for each voxel, is either specified by the user or a heuristic standard value is used. In this case, it is generally assumed that the greater the number of MR images recorded, and hence the longer the MR signal curve measured for the voxel, the greater the accuracy and the image quality.

SUMMARY OF THE INVENTION

An object of the present invention is to accelerate measurement with MR fingerprinting.

The present invention provides a method for the examination of a predetermined volume portion of an object with a magnetic resonance system. The method according to the invention includes the following steps.

An MR signal curve is acquired for each of multiple voxels of the volume portion.

The measured MR signal curve of the respective voxel is compared with stored MR signal curves in order to determine the stored MR signal curve that conforms most closely to the measured MR signal curve.

The result of the comparison is provided from the processor in which the comparison is implemented. The result of this comparison can be, for example, the n-tuple of physical values assigned to the MR signal curve determined and stored, or a substance assigned to this MR signal curve.

In accordance with the invention, use is made of the fact that, during the performance of the comparison, the MR signal curve of the respective voxel has a specific number of signal points, and each of these signal points was determined with reference to an MR measurement or an MR image. To assess the currently most closely conforming MR signal curves of the voxels, a quality measure is determined. If this quality measure is below a predetermined quality threshold value, the number of signal points of the MR signal curve of the corresponding voxel is increased by a predetermined difference number and the performance of the comparison is repeated with the MR signal curve of the corresponding voxel extended by the difference number.

While, according to the prior art, only one number of MR images or MR measurements (and hence the length of the measured MR signal curves) is prespecified, according to the invention an initial number is prespecified, the size of which is generally significantly below the prespecified number according to the prior art. If, on the basis of the measured MR signal curve, the length of which corresponds to the initial number (i.e. the number of signal points of the MR signal curve corresponds to the initial number), it is already possible to determine a sufficiently closely conforming stored MR signal curve, the search for this voxel can be successfully ended at this stage. The comparison of the measured MR signal curve with a length corresponding to the initial number or another still sub-maximum number is in particular performed with a stored MR signal curve in that the corresponding portion (same length and same measuring/simulation parameters as the measured MR signal curve) of the stored MR signal curve is used for the comparison. If, on the basis of the measured MR signal curve with a length corresponding to the initial number, it is not yet possible to determine a sufficiently closely conforming stored MR signal curve, the MR signal curve of the corresponding voxel is extended by the difference number and the comparison repeated with this extended MR signal curve. In this case, the (measured) MR signal curve of the voxel is so-to-speak extended until a stored MR signal curve conforms sufficiently closely to the MR signal curve of the voxel or until the quality measure is above the quality threshold value.

According to a preferred embodiment of the invention, to determine the quality measure, an MR image is reconstructed on the basis of the stored MR signal curves currently most closely conforming to the respective voxels and an image quality criterion calculated for this reconstructed MR image. Hence, with this embodiment, the image quality criterion corresponds to the quality measure, so that the method according to the invention is aborted if the current quality measure is above the desired quality threshold value, otherwise it is continued.

With reference to the currently most closely conforming MR signal curves (i.e. with reference to the fingerprints), it is possible to determine for each voxel, for example, a T1 relaxation time, a proton density or a portion of cerebral grey matter for the respective voxel. It is then possible to determine a pixel value on the basis of this physical value of the respective voxel and thereby to reconstruct an MR image. If a quality measure determined for this reconstructed MR image specific is sufficiently good (i.e. is above the quality threshold value), the method according to the invention can be successfully concluded.

The signal-to-noise ratio of the reconstructed MR image can be calculated as the image quality criterion for example. If this signal-to-noise ratio is above a predetermined signal-to-noise ratio-threshold value (i.e. the reconstructed MR image has relatively little noise), the reconstructed MR image will be considered to be sufficiently good and so the method according to the invention can be successfully concluded.

According to a further embodiment according to the invention, a sparsifying transformation (e.g. a wavelet transformation) is performed for the reconstructed MR image. With this embodiment, the image quality criterion is defined as a measure of the sparsity of the transformed MR image. The quality threshold value is equated to a predetermined threshold value so that the method according to the invention is successfully concluded when the sparsity measure is above the sparsity threshold value.

As used herein, sparsity means scarcity, i.e. a sparse or only scattered arrangement of, for example, pixels. Consequently, a sparsifying transformation means a transformation resulting in more pronounced sparsity. Consequently, the sparsifying transformation of the reconstructed MR image results in the production of an image with more pronounced sparsity than the sparsity of the reconstructed MR image. The sparsity or the sparsity measure of the transformed image, can be determined, for example, with reference to the L1 standard for the transformed image. If this sparsity measure is above the sparsity threshold value, i.e. if the sparsity of the transformed image is sufficient, the method according to the invention is successfully concluded.

According to the invention it is also possible, during the performance of the comparison of the measured MR signal curve with the stored MR signal curves, to determine a degree of conformity between the measured MR signal curve of the voxel and the most closely conforming stored signal curve. This degree of conformity then corresponds to the quality measure and a predetermined conformity threshold value corresponds to the quality threshold value. If the degree of conformity is below the predetermined conformity threshold value, the number of signal points of the MR signal curve of the corresponding voxel is increased by the predetermined difference number and the performance of the comparison repeated with the MR signal curve of the corresponding voxel extended by the difference number.

The conformity threshold value and hence the required accuracy can be prespecified by the user. This specification can also take place indirectly for example in dependence on the accuracy with which specific physical values (T1 relaxation time, T2 relaxation time etc.) for the voxels are to be determined. At the same time, this accuracy requirement in turn depends upon the resolution with which the MR signal curves are stored with respect to the physical values. For example, the requirement to determine the T1 relaxation time to 1 ms and the T2 relaxation time to 10 ms precisely, can, in dependence on the resolution of the stored MR signal curves, which is 1 ms for both the T1 relaxation time and the T2 relaxation time, be converted to a corresponding conformity threshold value.

According to the invention, the degree of conformity can also be defined relatively. In this case, the degree of conformity or probability of conformity between the MR signal curve of the respective voxel and hence the most closely conforming stored MR signal is determined. This (best) degree of conformity is compared with the degree of conformity with which other stored MR signal curves conform to the MR signal curve of the respective voxel. If the difference between the best degree of conformity and the second best degree of conformity is below the conformity threshold value, the comparison is repeated with an extended MR signal curve of the voxel.

In this case, the determination of the degree of conformity can be performed with reference to a correlation analysis, e.g. with the so-called cosine similarity. To this end, an MR signal curve is treated as a vector, wherein the dimension of the vector corresponds to the length of the MR signal curve or the number of signal points and the respective component of the vector to the size of the MR signal. The stored MR signal curve with the greatest cosine similarity to the MR signal curve of the respective voxel conforms most closely to the MR signal curve of the voxel.

According to the invention, the length of the MR signal curves of the respective voxels and hence the complexity or the computing time for the determination of the most closely conforming stored MR signal curve for each voxel in each case can be reduced. If the search for the most closely conforming stored MR signal curve is performed simultaneously with the acquisition of the MR data (for the acquisition of the MR signal curves of the voxels), it is also possible to abort the step of the acquisition of the MR signal curves as soon as a sufficiently closely conforming stored MR signal curve has been determined for the voxels of the volume portion in each case. In other words, the present invention makes it possible to keep the measuring time for the acquisition of the MR signal curves of the voxels almost as optimally short as possible in that the length of the MR signal curves of the voxels is only selected as long enough to allow a sufficiently closely conforming stored MR signal curve per (relevant) voxel to be determined with the respective MR signal curve.

In this case, even if a sufficiently closely conforming stored MR signal curve could not be determined for all (relevant) voxels, the difference number by which the number of signal points is increased can be determined on the basis of convergence behavior and/or on the basis of the recording parameters with which the MR signal curves are determined.

According to this embodiment, the difference number is not constant but is adapted to the convergence behavior and/or to recording parameters. In this case, the convergence behavior determines how the degree of conformity of the MR signal curve of the respective voxel approaches the conformity threshold value. For example, the lower the difference between the current degree of conformity and the conformity threshold value, the lower the difference number can be determined. If the pseudo-random variation of the recording parameters for the acquisition the MR signal curves generates pronounced or marked MR signal curves, the difference number can be set lower than when this is not the case.

It is also possible to set the difference number as constant (e.g. to a value of 25).

The adaptation of the difference number to the convergence behavior and/or the recording parameter or measuring parameters enables the MR signal curves of the voxels and hence the measuring time to be reduced to virtually the optimal degree.

According to the invention, the measurement (i.e. the step of the acquisition of the MR signal curves) can be aborted as soon as the most closely conforming stored MR signal curve for has been determined for all relevant voxels with the required degree of accuracy. However, it is also possible to end the measurement as soon as a ratio between a number of voxels for which the degree of conformity is above the conformity threshold value and a number of the relevant voxels is above a predetermined ratio threshold value (e.g. 95%). In addition, the measurement can be ended when a prespecified maximum measuring time is exceeded or a prespecified maximum number of MR images has been acquired.

The predetermined abort criteria prevent the measurement from being aborted insufficiently early since, for example, it is not possible to determine conforming stored MR signal curves for voxels which have incorrectly been classed as relevant with the desired accuracy since the respective voxel is, for example, located in a noisy background.

Usually, the step of the performance of the comparison is no longer performed for those voxels for which the degree of conformity has already once exceeded the conformity threshold value in a previous comparison.

According to a preferred embodiment of the invention, only those voxels for which the corresponding MR signal lies above a noise are chosen as the voxels of the volume portion for each of which the most closely conforming stored MR signal curve is to be determined. In other words, according to this embodiment, the only voxels taken into account (as relevant) are those lying outside a noise and for which a genuine signal can be measured. No most closely conforming MR signal curve is determined for voxels for which only a noise signal is acquired.

According to the invention, the (relevant) voxels of the volume portion, for which a most closely conforming stored MR signal curve is to be determined can also, for example, be prespecified by a user.

In this case, these voxels can be specified in the form of a region or a mask, for example, so that the most closely conforming stored MR signal curve is determined for all voxels within this range or within this mask.

These voxels can be specified on the basis of application-specific previous knowledge and/or on the basis of a previously generated MR overview image.

The MR overview images can be used, for example, to extract landmarks in order to generate a corresponding mask on the basis of these landmarks. This enables the set of voxels to be restricted to the cartilage region of a joint. In the simplest case, the mask can be generated from the MR overview image by a threshold value operation in that this mask is generated, for example, from the pixels of the MR overview images with a pixel value greater than a predetermined pixel-value threshold value.

According to a further embodiment of the invention, sets of voxels are determined, wherein it is expected that, with each of these sets, the performance of the step of the comparison will result in a similar degree of conformity. For example, adjacent voxels, which according to an overview image belong to an image region of the same kind, can form a set of this kind. Then for each set, the step of the performance of the comparison will only be performed for a specific subset of voxels in the set (in an extreme case, for only one voxel in the set). Only when a ratio between the number of voxels in the subset, for which the degree of conformity is above the conformity threshold value, and the number of voxels in the subset is above a predetermined further ratio threshold value, will the step of the comparison also be performed for the remaining voxels in the respective set.

This further embodiment is based on the assumption that the degree of conformity between adjacent voxels in the same image region only differs slightly. This further embodiment can further reduce the computing time of the method according to the invention in that the performance of the comparison is performed at greater intervals for the majority of the relevant voxels while only a part (the subset) of the respective set of voxels is checked more frequently. If a sufficiently closely conforming stored signal curve is assigned for a sufficiently large proportion of the voxels in the subset, the performance of the comparison for the rest of the voxels in the corresponding set can be performed successively or in one execution.

According to a further embodiment according to the invention, the currently provided result of the comparison is used to reconstruct and display an MR image. On the basis of this display, an operator will then be able to decide that the MR image is of sufficient quality so that at least the step of the acquisition of the MR signal curves is aborted. To reconstruct this MR image, the value of the respective voxel can be determined on the basis of the stored MR signal curve which was determined as most closely conforming for the respective voxel.

According to this embodiment, during the method according to the invention, a user will be shown an MR image reconstructed with the currently available accuracy for inspection, wherein the user is then able to decide on the basis of this MR image whether to abort a further measurement since he is already satisfied with the quality of the MR image.

However, at the end of the method according to the invention, the complete measured MR signal curve for each relevant pixel or voxel should be compared once again with the stored signal curves in order in each case to determine the most closely conforming stored MR signal curve. In this case, it is also possible to determine the respective most closely conforming stored MR signal curve for voxels with noisy MR signals or for voxels that are not specified as relevant.

Although, this last step of the method according to the invention does extend the reconstruction time, the accuracy is advantageously increased, since the comparison can be performed for each voxel with all the available data.

With the present invention, an MR signal curve is acquired for each of a plurality of voxels and compared with stored MR signal curves in order to determine the stored MR signal curve that conforms most closely with the measured MR signal curve. A quality measure is used to decide whether the stored MR signal curves determined result in a sufficiently good result or reconstructed MR image. This decision can be made in two ways On alternative is to determine the a degree of conformity between the measured MR signal curve and the most closely conforming stored MR signal curve for each voxel. If this degree of conformity determined for each voxel is sufficiently high, it is assumed that the result is sufficiently good.

Another alternative is to use the most closely conforming stored MR signal curves to determine a physical value (e.g. T1 relaxation time, proton density), and hence a value for each voxel, by which an MR image is (re)constructed. A quality measure is determined for this reconstructed MR image. If this quality measure is sufficiently good, it is assumed that the result is sufficiently good.

If the stored MR signal curves that have been determined produce a sufficiently good result, the method according to the invention is ended by these curves stored as MR signal curves that are used to reconstruct the MR image, or the reconstructed MR image is emitted as a data file as a result. If the stored MR signal curves determined do not result in a sufficiently good result, the MR signal curve measured for each voxel is extended and the determination of the respective stored MR signal curve that conforms most closely to the (extended) measured MR signal curve for each voxel repeated. This is continued until a sufficiently good result is obtained.

According to the invention, it is also possible to make the above decision in two ways, wherein the method according to the invention is (only) ended when both the degree of conformity determined for each voxel is sufficiently high and the reconstructed MR image has a sufficiently good quality measure.

The present invention also encompasses a magnetic resonance apparatus for the examination of a predetermined volume portion of an object. The magnetic resonance apparatus has a scanner with a basic field magnet, a gradient coil arrangement with a gradient control unit, an RF antenna system with an RF antenna control unit and a computer. The magnetic resonance scanner is designed to acquire an MR signal curve for a number of voxels of the volume portion in order to use a comparator of the computer to compare the MR signal curve of the respective voxel with MR signal curves stored in a database of the magnetic resonance apparatus in order to determine the stored MR signal curve that conforms most closely to the acquired MR signal curve of the respective voxel and to provide a result of this comparison. The comparison starts with the MR signal curve of the voxel with a specific number of signal points. The computer of the magnetic resonance apparatus determines a quality measure with which a quality of the most closely conforming stored MR signal curves is determined. If the quality measure is below a predetermined quality threshold value, the comparison for the respective voxel is repeated, with the number of signal points of the MR signal curve of the respective voxel being first increased by a difference number.

The advantages of the magnetic resonance apparatus according to the invention substantially correspond to the advantages of the method according to the invention as explained in detail above.

The present invention also encompasses a non-transitory, computer-readable data storage medium encoded with programming instructions, which can be loaded into a memory of a programmable controller or a computer of a magnetic resonance apparatus. The programming instructions causes the computer or controller to implement all or several of the above-described embodiments of the method according to the invention when the programming instructions are executed in the controller or control mechanism of the magnetic resonance apparatus. The programming instructions may need programming means, e.g. libraries and auxiliary functions in order to implement the corresponding embodiments of the method. The programming instructions can be a source code (e.g. C++) that has still to be compiled (translated) and linked, or which only needs to be interpreted, or can be an executable software code that only needs to be loaded into the computer or controller to be executed.

The electronically readable data carrier can be, e.g. a DVD, a magnetic tape, a hard disk or a USB stick on which electronically readable control information is stored.

The present invention enables a determination to be automatically made during an MR fingerprinting examination as to when the measurement has reached a required (by the user) accuracy and thus can be ended. Thus, the present invention enables the measuring time of an MR fingerprinting examination to be reduced without having to change the quality of the measuring result. Similarly, the present invention enables the image reconstruction time (for example due to quicker database matching with the execution of pattern recognition), by making use of shorter signal curves than in the prior art, and to take into account only those relevant voxels for which to date no stored MR signal curve with the required accuracy has been determined.

DESCRIPTION OF THE PREFERRED EMBODIMENTS

Figure 1:
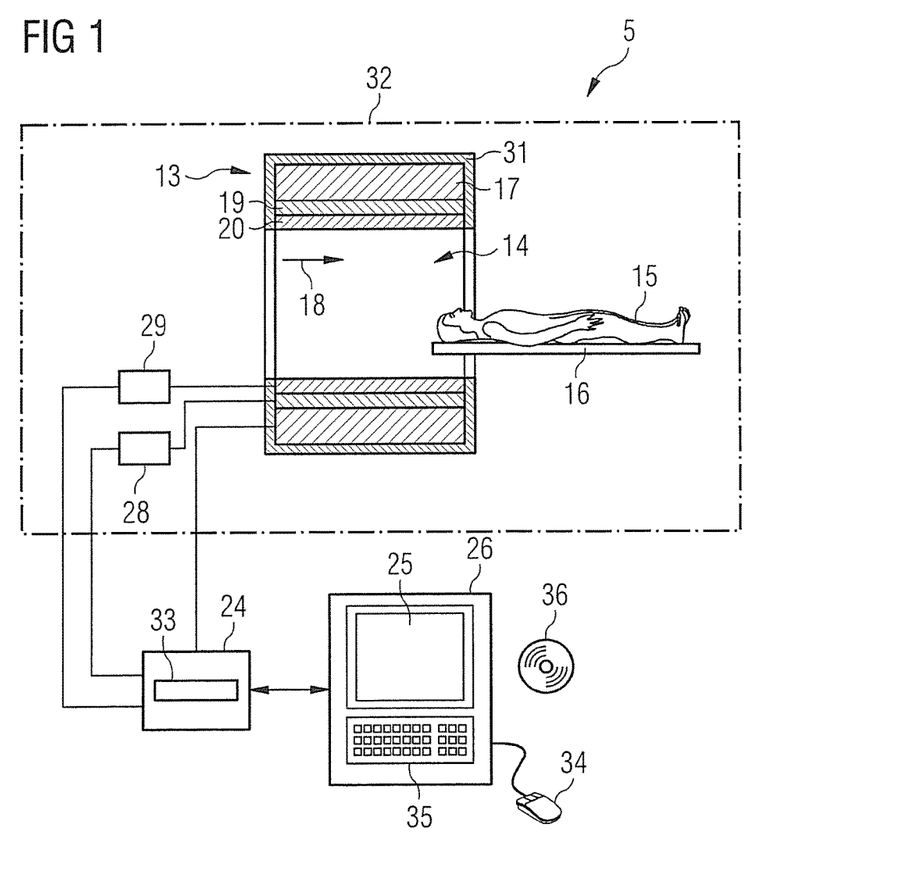
FIG. 1 schematically illustrates a magnetic resonance apparatus according to the invention.

FIG. 1 schematically shows a magnetic resonance apparatus 5 according to the invention. The magnetic resonance apparatus 5 has a scanner 13 with a basic field magnet 17 that generates a strong and constant basic magnetic field 18. The scanner 13 also has a cylindrical patient-receiving area 14 to receive an object under examination 15, in the present case a patient 15. The patient-receiving area 14 is surrounded circumferentially by the scanner 13 in a cylindrical shape. The patient 15 can be moved into the patient-receiving area 14 by a patient support 16 of the magnetic resonance apparatus 5. To this end, the patient support 16 has a table arranged movably within the scanner 13. The scanner 13 is shielded from the exterior by a housing shell 31.

The scanner 13 further has a gradient coil arrangement 19 that generates magnetic gradient fields for spatial encoding during imaging. The gradient coil arrangement 19 is controlled by a gradient control unit 28.

The scanner 13 also has a radio-frequency (RF) antenna unit 20, which, in the case shown, is a body coil permanently integrated in the scanner 13, and a radio-frequency antenna control unit 29 to excite nuclear spins in the object 15 to cause them to deviate from the polarization that is established in the basic magnetic field 18 generated by the basic field magnet 17. The radio-frequency antenna unit 20 is controlled by the radio-frequency antenna control unit 29 and emits radio-frequency magnetic resonance sequences in an examination chamber substantially formed by the patient-receiving area 14. The radio-frequency antenna unit 20 is also embodied to receive magnetic resonance signals from the patient 15.

To control the basic field magnet 17, the gradient control unit 28 and the radio-frequency antenna control unit 29, the magnetic resonance apparatus 5 has a computer 24. The computer 24 centrally controls the magnetic resonance apparatus 5, such as for the performance of a predetermined imaging gradient-echo sequence. Control information such as imaging parameters, and reconstructed MR images can be provided to a user via a user interface, which in the present case is a display monitor 25. The magnetic resonance apparatus 5 also has an input unit 26 via means of which information and/or parameters can be entered during a measuring process by a user. The computer 24 can include the gradient control unit 28 and/or radio-frequency antenna control unit 29 and/or the display monitor 25 and/or the input unit 26.

In the case shown, the computer 24 has a comparison unit 33.

The magnetic resonance apparatus 5 further has a signal curve acquisition unit 32. In the present case, the signal curve acquisition unit 32 is formed by the scanner 13 with the radio-frequency antenna control unit 29 and the gradient control unit 28. Hence, the magnetic resonance apparatus 5 is designed together with the signal curve acquisition unit 32, the computer 24 and the interface to carry out the method according to the invention.

The choice of corresponding control programs for an MR fingerprinting examination, stored, for example, on a DVD 36 and the depiction of the results generated in this way takes place via the monitor 25. The input unit 26 includes a keyboard 15, a mouse 16 and the screen monitor 25.

The magnetic resonance apparatus 5 can have further components normally included in a magnetic resonance apparatus 5. The general mode of operation of a magnetic resonance apparatus 5 is known to those skilled in the art, so a detailed description of the further components is not necessary herein.

Figure 2:
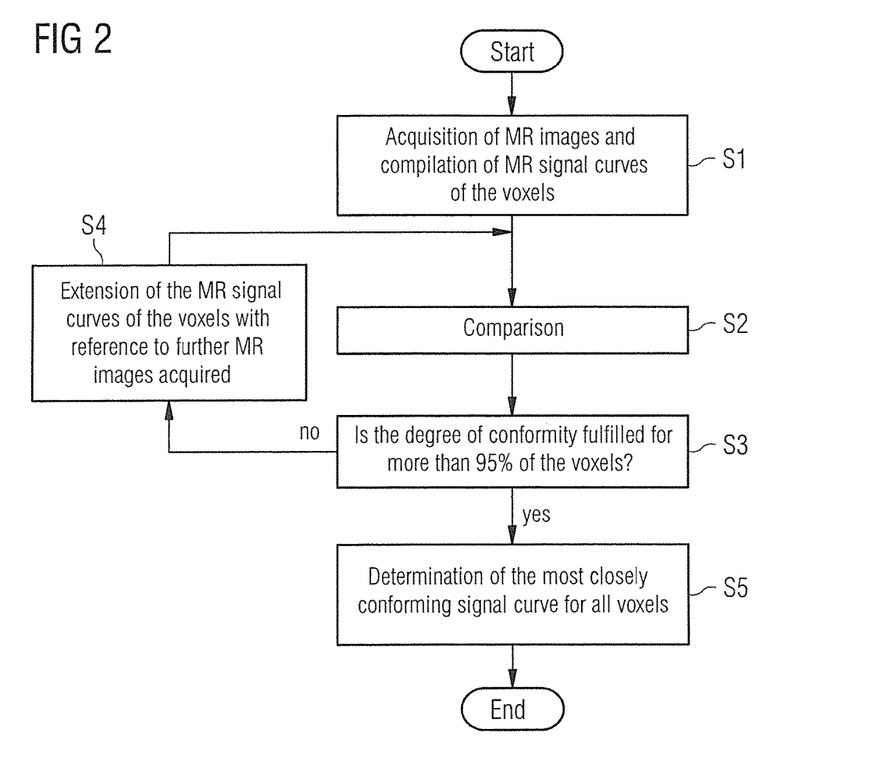
FIG. 2 is a flowchart of an embodiment according to the invention.

FIG. 2 shows a flowchart of an embodiment according to the invention.

In a first step S1, MR data is acquired and with reference to this MR data, MR signal curves are compiled for a plurality of voxels in a volume portion under consideration of an object under examination. In this case, the length of the MR signal curves of the voxels corresponds to an initial predetermined number (e.g. 50) of signal points or MR images, which are acquired by a slice in which the respective voxel is located. This initial predetermined number can correspond to a measuring time, which is necessary is in order to acquire the corresponding MR data of a predetermined volume portion of an object under examination in order to determine the MR signal curves of the voxels of an initial length (or of the initial predetermined number of signal points) with reference to this MR data.

For example, in Step S1, it is possible to prespecify a required accuracy with which a measured MR signal curve should conform to the most closely matching stored MR signal curve. This required accuracy can either be prespecified by the user or determined on the basis of the resolution of the stored MR signal curves with respect to a physical value (e.g. T1 relaxation time, T2 relaxation time). In Step S1, it is also possible to prespecify an image region in which the pixels or voxels of interest are located. Similarly, in Step S1 it is possible to prespecify an automatism or algorithm with reference to which the pixels or voxels of interest are determined. If voxels of interest are determined, in the following steps, the most closely matching stored MR signal curve is only sought for the voxels in this image region.

In a second step S2, a comparison of the MR signal curve of the respective voxel with stored MR signal curves will be performed for at least a specific part of the voxels. The object of this comparison is to find the stored MR signal curve conforming most closely to the MR signal curve measured for the respective voxel. If the conformity between this most closely matching stored MR signal curve and the measured MR signal curve satisfies a required accuracy, the respective voxel is marked 'finished'. In other words, a check is performed as to whether the degree of conformity between the MR signal curve measured for the respective voxel and the most closely matching stored MR signal curve is above a conformity threshold value, wherein the result of this comparison of the degree of conformity for the respective voxel is stored. In Step S2, a measured MR signal curve is only compared with the stored MR signal curves for voxels which are not yet classified as 'finished'.

The comparison of the MR signal curves can be performed by means of a common pattern recognition method and/or by means of correlation analysis.

In the third step, Step S3, a check is performed as to whether the degree of conformity is fulfilled for more than a predetermined percentage (e.g. 95%). If this is the case, the method according to the invention passes through Step S5 and is ended. However, if this is not yet the case, the MR signal curves are extended with reference to further acquired MR data or MR images in Step S4.

Accordingly, the acquisition of MR images is initiated (see Step S1). If a sufficient number of MR images is acquired for the MR signal curves of the voxels to have the initial length, the first comparisons of the measured MR signal curves with the stored MR signal curves are performed. In this time, the acquisition of MR data, and hence the acquisition of MR images reconstructed with reference to this MR data, is continued in order in this way to extend the MR signal curves of the voxels. This enables the performance of later comparisons with extended MR signal curves as a result of which, as a rule, the degree of conformity between the respective measured MR signal curve and the stored MR signal curve most closely matching this measured MR signal curve is improved with respect to a comparison with a shorter measured MR signal curve. The acquisition of (further) MR data or MR images is aborted or the user is informed that the measurement can be aborted if a sufficiently large proportion of the voxels can be assigned to one of the stored MR signal curves with a sufficiently high degree of accuracy.

Optionally, at the end of the method according to the invention, in Step S5, for each voxel (of interest) it is possible to determine (again) the stored MR signal curve which conforms most closely to the measured MR signal curve of the respective voxel. As a result it is advantageously possible for better results to be obtained for voxels for which the associated stored MR signal curve was determined with reference to a relatively short MR signal curve since the search for the most closely matching stored MR signal curve can now be performed for each voxel with the longest available measured MR signal curve.

Figure 3:
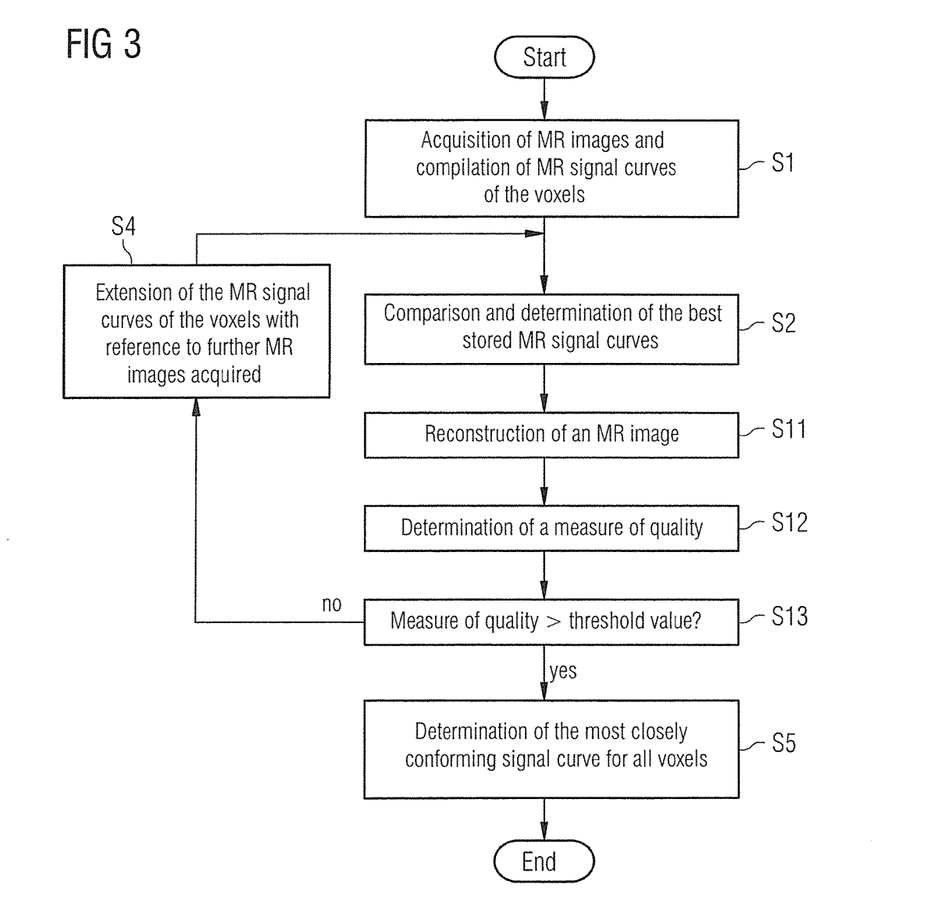
FIG. 3 is a flowchart of another embodiment according to the invention.

FIG. 3 shows another embodiment according to the invention. In FIG. 3, steps (substantially) corresponding to the steps of the embodiment shown in FIG. 2 are given the same reference numbers.

As in the embodiment shown in FIG. 2, in Step S1, MR images are acquired and MR signal curves of the voxels compiled. Similarly to the embodiment shown FIG. 2, in Step S2, for every voxel, the measured MR signal curve is compared to the stored MR signal curves in order to determine for each voxel the stored MR signal curve most closely conforming with the measured MR signal curve.

In Step S11, the stored MR signal curves conforming most closely to the measured MR signal curves are used to reconstruct an MR image. To this end, the physical value (e.g. T1 relaxation time, proton density) corresponding to the corresponding stored MR signal curve for the respective voxel is used to determine a pixel value of the respective voxel and the MR image is generated thereby.

For the reconstructed MR image a signal-to-noise ratio of the reconstructed MR image or a sparsity criterion, for example, is used to determine a quality measure for the reconstructed MR image. In the following step, S13, a check is performed as to whether this quality measure is above a predetermined quality threshold value. If this is the case (i.e. if the reconstructed MR image is of sufficient quality), the method according to the invention is ended. Otherwise, the MR signal curves of the voxels are extended, as is also the case with the embodiment shown in FIG. 2.

Optionally, Step S5 can also be carried out for the embodiment shown in FIG. 3 Step S5 in order to determine for each voxel the stored MR signal curve that conforms most closely to the measured MR signal curve of the respective voxel.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for magnetic resonance (MR) fingerprinting comprising:
    operating an MR scanner, while a subject is situated therein, to acquire MR data and generating an MR signal curve for voxels of a volume within the examination subject based on the MR data, the MR signal curve having a predetermined number of signal points;
    providing said MR signal curve to a processor and, in said processor, comparing said MR signal curve for a respective voxel with a plurality of stored MR signal curves, to determine a stored MR signal curve, among said plurality of stored MR signal curves, that conforms most closely to the MR signal curve of the respective voxel, by implementing said comparison of said MR signal curve with said plurality of stored MR signal curves only for the predetermined number of signal points;
    in said processor, determining a quality measure that designates a quality of said most closely conforming stored MR signal curves;
    if said quality measure is below a predetermined quality threshold value, adjusting the MR signal curve by a predetermined difference number and repeating comparison of said MR signal curve of the respective voxel with said plurality of stored MR signal curves and, for each repetition of said comparison, increasing said number of signal points included in the MR signal curve and used in the comparison by the predetermined difference number;
    when said quality measure reaches said quality threshold value, making the most closely conforming stored MR signal curve for which said quality measure reaches said quality threshold value available as an electronic signal from said processor; and
    determining said quality measure by reconstructing an MR image using respective stored MR signal curves that respectively conform most closely to the MR signal curve for respective voxels of said volume, and calculating an image quality criterion for said reconstructed MR image, and using said image quality criterion as said quality measure.

2. A method as claimed in claim 1 comprising determining said image quality criterion as a signal-to-noise ratio of said reconstructed MR image, and using a predetermined signal-to-noise ratio threshold value as said quality threshold value.

3. A method as claimed in claim 1 comprising:
    subjecting said reconstructed MR image to a sparsifying transformation, thereby obtaining a transformed MR image;
    measuring a sparsity of said transformed MR image and using said sparsity as said image quality criterion; and
    using a predetermined sparsity threshold value as said quality threshold value.

4. A method as claimed in claim 1 comprising:
    determining said quality measure as a determination of a degree of conformity between the MR signal curve of a respective voxel and the stored MR signal curve most closely conforming thereto; and
    using a predetermined conformity threshold value as said quality threshold value.

5. A method as claimed in claim 4 comprising:
    predetermining said difference number by matching said difference number of signal points to at least one of convergence behavior and a data acquisition parameter with which said MR signal curve is acquired for each voxel, said convergence behavior determining how said degree of conformity of the respective voxel corresponds to said conformity threshold value.

6. A method as claimed in claim 4 comprising operating said MR scanner to abort acquisition of said MR signal curve for voxels of said volume as soon as a ratio between a number of voxels for which said degree of conformity is above said conformity threshold value, and a number of voxels for which said most closely conforming stored MR signal curve is above a predetermined ratio threshold value.

7. A method as claimed in claim 4 comprising ceasing performance of said comparison for voxels for which said degree of conformity has already once been determined to be above said conformity threshold value.

8. A method as claimed in claim 4 comprising, in said processor:
    determining sets of voxels for which there is an expectation that said comparison will result in a similar degree of conformity;
    performing said comparison for only one subset of voxels among said sets; and
    also performing said comparison for remaining voxels of said set when a ratio between a number of voxels in the subset for which the degree of conformity is above the threshold value, and a number of voxels in the subset, is above a predetermined further ratio threshold value.

9. A method as claimed in claim 1 comprising using only voxels for said comparison for which an MR signal of the acquired MR signal curve thereof is higher than a predetermined noise signal level.

10. A method as claimed in claim 1 comprising using only predetermined voxels, among all of said voxels in said volume, for said comparison.

11. A method as claimed in claim 10 comprising predetermining said number of voxels for use in said comparison dependent on a criterion associated with examination of said subject, or dependent on a previously generated MR overview image of the subject.

12. A method as claimed in claim 1 comprising using said most closely conforming stored MR signal curve represented in said electronic signal to reconstruct an MR image of the subject and displaying said MR image at a display monitor in communication with said processor, and allowing further acquisition of said MR signal curve from said volume to be aborted dependent on a review of said MR image at said display monitor.

13. A method as claimed in claim 1 comprising, at an end of a complete MR signal curve, comparing each voxel again with said stored MR signal curves to determine said most closely conforming stored MR signal curves.

14. A magnetic resonance (MR) apparatus comprising:
an MR scanner;
a control computer configured to operate said MR scanner, while a subject is situated therein, to acquire MR data and to generate an MR signal curve for voxels of a volume within the examination subject based on the MR data, the MR signal curve having a predetermined number of signal points;
a processor provided with said MR signal curve, said processor being configured to compare said MR signal curve for a respective voxel with a plurality of stored MR signal curves, to determine a stored MR signal curve, among said plurality of stored MR signal curves, that conforms most closely to the MR signal curve of the respective voxel, by implementing said comparison of said MR signal curve with said plurality of stored MR signal curves only for the predetermined number of signal points;
said processor being configured to determine a quality measure that designates a quality of said most closely conforming stored MR signal curves;
said processor being configured to, if said quality measure is below a predetermined quality threshold value, adjust the MR signal curve by a predetermined difference number and repeat comparison of said MR signal curve of the respective voxel with said plurality of stored MR signal curves and, for each repetition of said comparison, increase said number of signal points included in the MR signal curve and used in the comparison by a predetermined difference number;
said processor being configured to determine when said quality measure reaches said quality threshold value, and then to make the most closely conforming stored MR signal curve for which said quality measure reaches said quality threshold value available as an electronic signal from said processor; and
said processor being configured to determine said quality measure by reconstructing an MR image using respective stored MR signal curves that respectively conform most closely to the MR signal curve for respective voxels of said volume, and calculating an image quality criterion for said reconstructed MR image, and using said image quality criterion as said quality measure.

15. A non-transitory, computer-readable data storage medium encoded with programming instructions, said storage medium being loaded into a control and evaluation computer of a magnetic resonance (MR) apparatus, comprising an MR scanner, said programming instructions causing said control and evaluation computer to:
operate an MR scanner, while a subject is situated therein, to acquire MR data and to generate an MR signal curve for voxels of a volume within the examination subject based on the MR data, the MR signal curve having a predetermined number of signal points;
compare said MR signal curve for a respective voxel with a plurality of stored MR signal curves, to determine a stored MR signal curve, among said plurality of stored MR signal curves, that conforms most closely to the MR signal curve of the respective voxel, by implementing said comparison of said MR signal curve with said plurality of stored MR signal curves only for the predetermined number of signal points;
determine a quality measure that designates a quality of said most closely conforming stored MR signal curves;
if said quality measure is below a predetermined quality threshold value, adjust the MR signal curve by a predetermined difference number and repeat comparison of said MR signal curve of the respective voxel with said plurality of stored MR signal curves and, for each repetition of said comparison, increase said number of signal points included in the MR signal curve and used in the comparison by a predetermined difference number;
when said quality measure reaches said quality threshold value, make the most closely conforming stored MR signal curve for which said quality measure reaches said quality threshold value available as an electronic signal from said control and evaluation computer; and
determine said quality measure by reconstructing an MR image using respective stored MR signal curves that respectively conform most closely to the MR signal curve for respective voxels of said volume, and calculating an image quality criterion for said reconstructed MR image, and using said image quality criterion as said quality measure.

* * * * *